(12) United States Patent
Lee et al.

(10) Patent No.: US 12,702,300 B2
(45) Date of Patent: Aug. 11, 2026

(54) NON-CONTACT MRI IN-BORE MOTION SENSING METHOD USING CW DOPPLER RADAR WITH BAND-PASS FILTERING

(71) Applicant: The Board of Trustees of the Leland Stanford Junior University, Stanford, CA (US)

(72) Inventors: Wonje Lee, Palo Alto, CA (US); Greig C. Scott, Mountain View, CA (US); John M. Pauly, Stanford, CA (US); Shreyas S. Vasanawala, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 12 days.

(21) Appl. No.: 18/202,577

(22) Filed: May 26, 2023

(65) Prior Publication Data

US 2023/0380689 A1 Nov. 30, 2023

Related U.S. Application Data

(60) Provisional application No. 63/346,273, filed on May 26, 2022.

(51) Int. Cl.
*A61B 5/00* (2006.01)
*A61B 5/0205* (2006.01)
(Continued)

(52) U.S. Cl.
CPC .......... *A61B 5/0035* (2013.01); *A61B 5/0205* (2013.01); *A61B 5/0507* (2013.01);
(Continued)

(58) Field of Classification Search
CPC ..... A61B 5/055; A61B 5/0035; A61B 5/0205; A61B 5/0507; A61B 5/0816;
(Continued)

(56) References Cited

U.S. PATENT DOCUMENTS 8,454,528 B2 6/2013 Yuen
8,754,772 B2 6/2014 Horng
(Continued)

OTHER PUBLICATIONS

Thiel, F. (2012). Evaluation elektromagnetischer Breitband-Sensoren für biomedizinische Anwendungen (Doctoral dissertation). (Year: 2012).*

(Continued)

*Primary Examiner* — Keith M Raymond
*Assistant Examiner* — Johnathan Maynard
(74) *Attorney, Agent, or Firm* — LUMEN PATENT FIRM

(57) ABSTRACT

Noncontact sensing of subject motion using Doppler radar within a magnetic resonance imaging (MRI) apparatus transmits a band-pass filtered continuous wave radio signal at a microwave frequency and receives a band-pass filtered reflected radio signal. The subject motion is detected from the received band-pass filtered reflected radio signal using a quadrature radio receiver with a software defined radio implementing Doppler radar. A first antenna, used for transmission and reception, is connected to the quadrature radio using band-pass filters and an RF coupler. A second antenna, used for reception, is connected directly to the quadrature radio using band-pass filters. The antennas are positioned in a bore of the MRI apparatus.

8 Claims, 13 Drawing Sheets

(51) Int. Cl.
*A61B 5/0507* (2021.01)
*A61B 5/055* (2006.01)
*A61B 5/08* (2006.01)
*A61B 5/113* (2006.01)

(52) U.S. Cl.
CPC ............ *A61B 5/055* (2013.01); *A61B 5/0816* (2013.01); *A61B 5/1135* (2013.01); *A61B 5/725* (2013.01); *A61B 5/7289* (2013.01)

(58) Field of Classification Search
CPC ..... A61B 5/1135; A61B 5/725; A61B 5/7289; A61B 5/024; A61B 5/05; G01S 13/88; G01S 7/358; G01S 7/2886; G01S 13/583; G01S 7/415; G01S 13/50; G01S 13/87; G01S 7/003; G01S 13/536
See application file for complete search history.

(56) References Cited

U.S. PATENT DOCUMENTS

| | | | | |
|---|---|---|---|---|
| 8,994,536 | B2 | 3/2015 | Margon | |
| 9,035,775 | B2 | 5/2015 | Margon | |
| 10,436,888 | B2 | 10/2019 | Li | |
| 11,051,702 | B2 | 7/2021 | Lin | |
| 11,350,849 | B2 | 6/2022 | Nakata | |
| 11,614,516 | B2 | 3/2023 | Santra | |
| 2008/0238757 | A1* | 10/2008 | Lin | G01S 13/38 600/407 |
| 2009/0278728 | A1 | 11/2009 | Morgan | |
| 2013/0165770 | A1* | 6/2013 | Li | A61N 5/1067 600/430 |
| 2015/0002331 | A1* | 1/2015 | Allmendinger | A61B 5/113 600/595 |
| 2015/0065857 | A1* | 3/2015 | Biber | A61B 5/0816 600/407 |
| 2015/0320342 | A1* | 11/2015 | Biber | A61B 5/055 324/318 |
| 2018/0235481 | A1* | 8/2018 | Liu | A61B 5/0205 |
| 2018/0353140 | A1* | 12/2018 | Speier | A61B 5/055 |
| 2018/0368803 | A1* | 12/2018 | Kording | A61B 8/02 |
| 2020/0341133 | A1* | 10/2020 | Chen | G01S 13/536 |
| 2021/0121131 | A1* | 4/2021 | Biber | A61B 5/113 |
| 2021/0325525 | A1* | 10/2021 | Biber | G01S 13/62 |
| 2022/0361822 | A1* | 11/2022 | Speier | G01R 33/5673 |

OTHER PUBLICATIONS

Thiel, F. (2010). Evaluation elektromagnetischer Breitband-Sensoren für biomedizinische Anwendungen (Doctoral dissertation). (Year: 2010).*

Thiel, F., Hein, M., Schwarz, U., Sachs, J., & Seifert, F. (2009). Combining magnetic resonance imaging and ultrawideband radar: A new concept for multimodal biomedical imaging. Review of Scientific Instruments, 80(1). (Year: 2009).*

Thiel, F., Kreiseler, D., & Seifert, F. (2009). Non-contact detection of myocardium's mechanical activity by ultrawideband RF-radar and interpretation applying electrocardiography. Review of Scientific Instruments, 80(11). (Year: 2009).*

Thiel, F., Helbig, M., Schwarz, U., Geyer, C., Rimkus, G., Kaiser, W. A., . . . & Seifert, F. (2009). Implementation of ultra-wideband sensors for biomedical applications. Frequenz, 63(9-10), 221-224. (Year: 2009).*

Thiel, F., Hein, M., Sachs, J., Schwarz, U., & Seifert, F. (Sep. 2008). Physiological signatures monitored by ultra-wideband-radar validated by magnetic resonance imaging. In 2008 IEEE International Conference on Ultra-Wideband (vol. 1, pp. 105-108). IEEE. (Year: 2008).*

Pramudita, A. A., & Suratman, F. Y. (2021). Low-power radar system for noncontact human respiration sensor. IEEE Transactions on Instrumentation and Measurement, 70, 1-15. (Year: 2021).*

Mostafanezhad, I., & Boric-Lubecke, O. (2014). Benefits of coherent low-IF for vital signs monitoring using Doppler radar. IEEE Transactions on Microwave Theory and Techniques, 62(10), 2481-2487. (Year: 2014).*

Mostafanezhad, I., Boric-Lubecke, O., & Lubecke, V. (Jan. 2010). A coherent low IF receiver architecture for Doppler radar motion detector used in life signs monitoring. In 2010 IEEE Radio and Wireless Symposium (RWS) (pp. 571-574). IEEE. (Year: 2010).*

Li, C., Peng, Z., Huang, T. Y., Fan, T., Wang, F. K., Horng, T. S., . . . & Lin, J. (2017). A review on recent progress of portable short-range noncontact microwave radar systems. IEEE Transactions on Microwave Theory and Techniques, 65(5), 1692-1706. (Year: 2017).*

Li, C., Lubecke, V. M., Boric-Lubecke, O., & Lin, J. (2013). A review on recent advances in Doppler radar sensors for noncontact healthcare monitoring. IEEE Transactions on microwave theory and techniques, 61(5), 2046-2060. (Year: 2013).*

Lee, W., Ryu, K., Robb, F., Pauly, J., Vasanawala, S., & Scott, G. (2022). Noncontact in-bore cardiopulmonary sensing using CW doppler radar. (Year: 2022).*

Kosch, O., Thiel, F., Seifert, F., Sachs, J., & Hein, M. A. (Sep. 2012). Motion detection In-Vivo by multi-channel ultrawideband radar. In 2012 IEEE International Conference on Ultra-Wideband (pp. 392-396). IEEE. (Year: 2012).*

Kontou, P., Smida, S. B., Daskalakis, S. N., Nikolaou, S., Dragone, M., & Anagnostou, D. E. (Jan. 2021). Heartbeat and respiration detection using a low complexity cw radar system. In 2020 50th European Microwave Conference (EuMC) (pp. 929-932). IEEE. (Year: 2021).*

Jensen, B. S., Jónasson, S. Þ., Johansen, T. K., & Jensen, T. (Oct. 2012). Vital signs detection radar using low intermediate-frequency architecture and single-sideband transmission. In 2012 9th European Radar Conference (pp. 67-70). IEEE. (Year: 2012).*

Gu, C., Li, R., Zhang, H., Fung, A. Y., Torres, C., Jiang, S. B., & Li, C. (2012). Accurate respiration measurement using DC-coupled continuous-wave radar sensor for motion-adaptive cancer radiotherapy. IEEE Transactions on biomedical engineering, 59(11), 3117-3123. (Year: 2012).*

Gu, C., Peng, Z., & Li, C. (2016). High-precision motion detection using low-complexity Doppler radar with digital post-distortion technique. IEEE Transactions on Microwave Theory and Techniques, 64(3), 961-971. (Year: 2016).*

Gu, C. (2016). Short-range noncontact sensors for healthcare and other emerging applications: A review. Sensors, 16(8), 1169. (Year: 2016).*

Ahmad, S. F., Kim, Y. C., Choi, I. C., & Kim, H. D. (2020). Recent progress in birdcage RF coil technology for MRI system. Diagnostics 10 (12): 1017. (Year: 2020).*

Yamada, S., Chen, M., & Lubecke, V. (Dec. 2006). Sub-μW signal power doppler radar heart rate detection. In 2006 Asia-Pacific Microwave Conference (pp. 51-54). IEEE. (Year: 2006).*

Gu, C., Li, C., Lin, J., Long, J., Huangfu, J., & Ran, L. (2009). Instrument-based noncontact Doppler radar vital sign detection system using heterodyne digital quadrature demodulation architecture. IEEE Transactions on Instrumentation and Measurement, 59 (6), 1580-1588. (Year: 2009).*

Wu, P. H., Jau, J. K., Li, C. J., Horng, T. S., & Hsu, P. (2012). Phase-and self-injection-locked radar for detecting vital signs with efficient elimination of DC offsets and null points. IEEE transactions on microwave theory and techniques, 61(1), 685-695. (Year: 2012).*

Thiel, et al., "Combining magnetic resonance imaging and ultrawideband radar: A new concept for multimodal biomedical imaging," Review of scientific instruments, vol. 80, No. 1, p. 014302, Jan. 2009.

Liu et al., "Non-contact non-invasive heart and respiration rates monitoring with mimo radar sensing," 2018 IEEE Global Communications Conference (GLOBECOM), ID: 3, 2018, pp. 1-6.

Buikman et al., The rf coil as a sensitive motion detector for magnetic resonance imaging. Magn Reson Imaging. May-Jun. 1988;6(3):281-9.

(56) References Cited

OTHER PUBLICATIONS

Lee et al.,Noncontact in-bore cardiopulmonary sensing using CW doppler radar. Abstract. ISMRM-ESMRMB ISMRT 31st Annual Meeting, London, England, May 7, 2022.

* cited by examiner

Bi-quad
displacement
Duke
Birdcage (B) Locus of Γ
0.1
0.05
0
-0.05
-0.1
-0.1
-0.05
0
0.05
0.1
Im(Γ-Γdc)
Re(Γ-Γdc)
(D) Local SAR vertical profile
0.44μW/kg
0
-10
-20
-30
-40
-50
-60
-70
[dB]
Duke Back surface
Duke Front surface
0
50
100
150
200
vertical distance [mm]

Antennas
112
114
SDR
110
Computer
BPFs
Cir.
RF cables
Ferrite cores & baluns
110

SDR
110
102
108
Cirulator
BPF
BPF
BPF
106
104
114
112
116
Antennas

*Fig. 3B*

```
% Pseudo code for phase demodulation

% DC offset correction
% Solve x = [a; b; r^2-a^2-b^2 ] to minimize |Ax-b|
% Where, A = [2R 2I 1]_Nsx3, b = [R^2 + I^2]_Nsx1
% Ns: # of samples
R = real(IQ); I = imag(IQ);
x = inv(A'*A)*A'*b;
Rc = R – a; % compensated real data
Ic = I – b; % compensated imag data

% phase demodulated signal
Ph_dem = unwrap(angle(complex(Rc,Ic)));
```

*Fig. 3C*

```
% Pseudo code for linear demodulation

% Voltage drift correction
cM = [Rc,Ic]; % DC offset corrected data
cMf = highpass(cM,0.5,samplerate);
% Linear demodulated signal
[COEFF, Y, LATENT] = pca(cMf);
Ln_dem = Y(:,1);

% SSA sub-function for peak detection
% WL: # of data samples within window length
% PC: number of combining PCs
SSA = ssa_fun(Ln_dem,WL,PC);
```

Front
Ch1 Ch2
(TRx) (Rx)
Free breathing
ch1(TRx) ch2(Rx)
[norm. scale]
Breath holding Left Side
Free breathing
TRx
Rx
[normal. scale]
Breath holding
Rx
TRx Back
Free breathing
[norm. scale]
Breath holding Sternum
Umbilicus
Free breathing @Umbilicus
[norm. scale]
Free breathing @Sternum
TRx
Rx
0 5 10 15 20
sec (A) PCA
×10-3
[Volts]
PC1
PC2

(B) SSA
[Norm. scale]
SSAPC1
ECG (C) SSA zoom in
[Norm. scale]
High PSSA
Low PSSA
PECG (D) Heartbeat rate
[Hz]
SSA
ECG
sec 4.9

4.8

4.8

*Fig. 8A* *Fig. 8B*
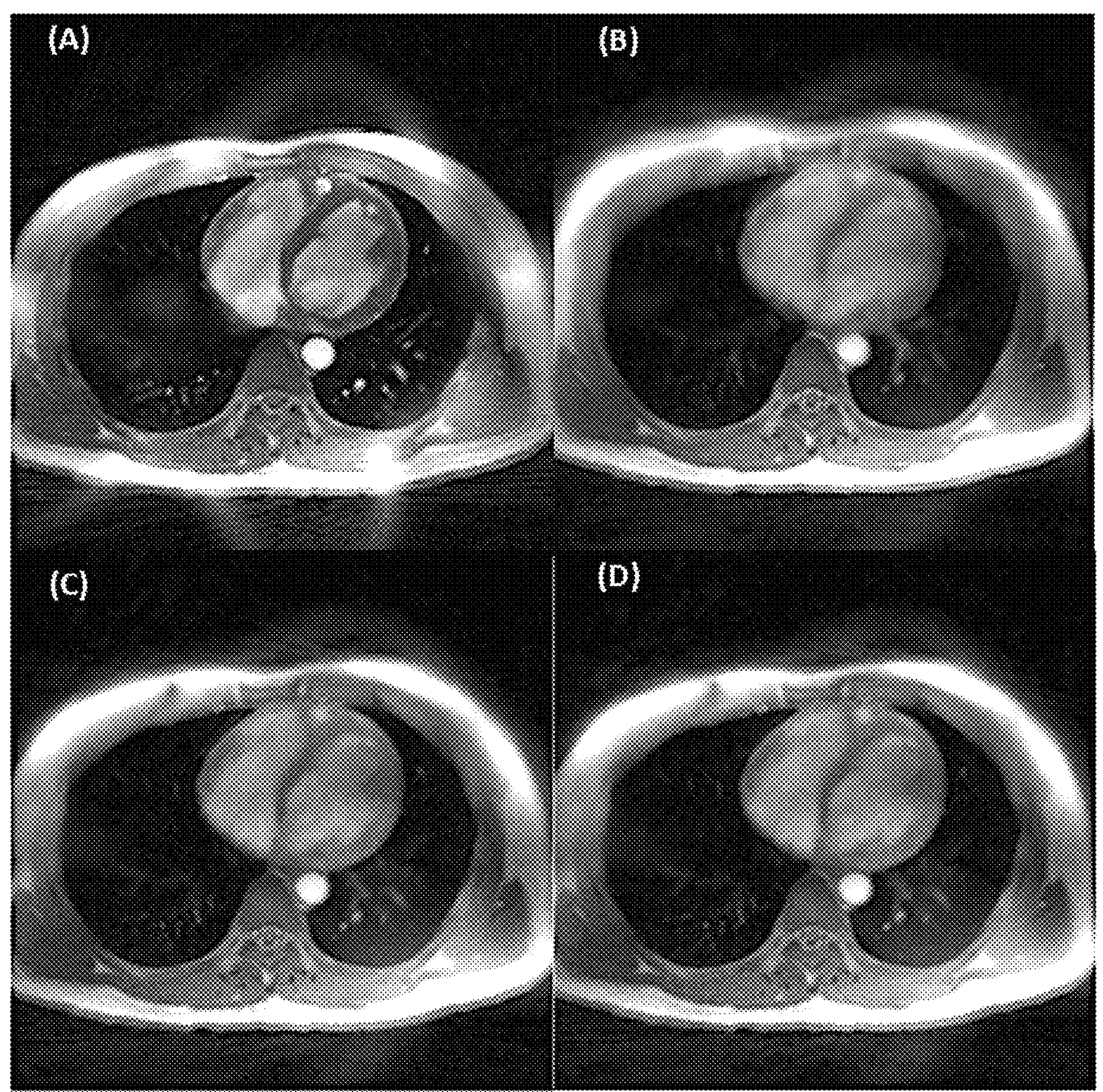
*Fig. 8C* *Fig. 8D*

NON-CONTACT MRI IN-BORE MOTION SENSING METHOD USING CW DOPPLER RADAR WITH BAND-PASS FILTERING

CROSS-REFERENCE TO RELATED APPLICATIONS

This application claims priority from U.S. Provisional Patent Application 63/346,273 filed May 26, 2022, which is incorporated herein by reference.

STATEMENT REGARDING FEDERALLY SPONSORED RESEARCH OR DEVELOPMENT

This invention was made with Government support under contract EB029427 awarded by the National Institutes of Health. The Government has certain rights in the invention.

FIELD OF THE INVENTION

The present invention relates generally to diagnostic imaging. More specifically, it relates to in-bore motion sensing techniques for magnetic resonance imaging.

BACKGROUND OF THE INVENTION

Subject motion in MRI has been problematic for decades and remains an active research field. Motion tracking data can be obtained using optical methods, field sensing methods, and MR navigators. Some of these approaches require external sensors such as accelerometers, fiducial markers, and acoustic sensors. Most are typically attached or mounted on a local displacement source, which may be a hindrance in routine clinical applications. Methods employing digital cameras can require optical registration points on a moving surface to track temporal displacement.

Non-contact motion detection methods would be highly preferred in MRI for better clinical throughput. Short-range radar has been of interest in healthcare vital signs sensing for decades. Of the many radar architectures, each has specific capabilities and limitations. For example, non-contact physiological motion sensing with ultra-wideband (UWB) pulsed radar has been used for vital sensing within the MRI bore. Continuous wave (CW) or Doppler radar would be desirable because it is capable of detecting heartbeat and respiration with a simpler system architecture, and with much less power. However, CW Doppler radar has not been adopted due to various challenges with integration into MRI, including interference of the CW Doppler radar signals with the strong time-varying EM fields in the MRI apparatus.

BRIEF SUMMARY OF THE INVENTION

Techniques of the present invention use a continuous wave (CW) Doppler radar with band-pass filter allocation in the radar front-end chain to provide MRI in-bore vital sensing. A circulator provides isolation between the receive and transmit signals. Band-pass filters (BPFs) mitigate MRI system interference caused by a portion of the RF peak power at kW levels leaking through the radar antenna and cables, with a detrimental effect on radar operation. BPFs are allocated at both Tx and Rx with minimum perturbation of antenna sensitivity. Putting a BPF right at the radar Tx port followed by the circulator provides isolation in transceiver antenna operation.

The techniques of the invention have application to diagnostic imaging including MRI, CT, or fusion systems for motion tracking or correction, and medical alert systems for patients, elderly, or infant monitoring purposes, where non-contact vital sensing is desired.

In one aspect, the invention provides a method using Doppler radar for noncontact sensing of subject motion within a magnetic resonance imaging (MRI) apparatus during an MRI scan. The method includes transmitting with a first antenna a band-pass filtered continuous wave radio signal at a microwave frequency; receiving with the first antenna and with a second antenna a band-pass filtered reflected radio signal; and detecting the subject motion from the received band-pass filtered reflected radio signal using a quadrature radio receiver comprising a software defined radio implementing Doppler radar. The first antenna is connected to the quadrature radio using band-pass filters and an RF coupler, and the second antenna is connected directly to the quadrature radio using band-pass filters. The first antenna and the second antenna are positioned in a bore of the MRI apparatus. The RF coupler may be a circulator, directional coupler, or hybrid coupler.

In one implementation, the first antenna is connected to the RF coupler, wherein a first band-pass filter is positioned between a transmission output of the quadrature radio and an input of the RF coupler, and a second band-pass filter is positioned between an output of the RF coupler and a reception input of the quadrature radio.

In another implementation, the second antenna is connected to a reception input of the quadrature radio, a third band-pass filter is positioned between the reception input of the quadrature radio and the second antenna, and the first band-pass filter, second band-pass filter, and third band-pass filter are configured to block MRI RF interference outside the radar operating frequency.

In one implementation, the transmitted band-pass filtered continuous wave radio signal is a low intermediate frequency modulated continuous wave radio signal. In this case, the received band-pass filtered reflected radio signal is a Doppler phase modulated intermediate frequency radio signal.

In another implementation, the transmitted band-pass filtered continuous wave radio signal is a monotone radio signal. In this case, the received band-pass filtered reflected radio signal is a Doppler phase modulated monotone radio signal. Preferably, the quadrature receiver uses a receiver local oscillator frequency that is offset from a transmit oscillator frequency. The receiver local oscillator frequency offset is preferably within a demodulation bandwidth of the software defined radio.

Preferably, the first antenna and the second antenna are directional antennas. The first antenna and the second antenna are preferably positioned symmetric with iso-center of a bore of the MRI apparatus, above a subject landmark (LM) position. The first antenna and the second antenna are preferably positioned on a bore of the MRI apparatus, above a target motion-sensing region. The first antenna and the second antenna are preferably positioned at a center circumferential line of a whole body volume coil between two adjacent rungs of a birdcage of the MRI apparatus, above a subject landmark position. The first antenna and the second antenna are preferably attached to a ceiling of a bore of the MRI apparatus. Alternatively, the first antenna and the second antenna may be embedded within a body coil of the MRI apparatus.

In one implementation, the transmitting and the receiving are triggered during the MRI scan by a scanner TTL control at start-of-scan. Preferably, the quadrature radio operates at power levels below 1 mW, more preferably below 1 μW.

BRIEF DESCRIPTION OF THE SEVERAL VIEWS OF THE DRAWINGS

FIGS. 3B, 3C show pseudocode for performing phase or linear demodulation, respectively.

FIGS. 7A, 7B, 7C are plots of noise covariance matrices and SNR for three respective scenarios: without the radar system, with the radar transmitter off, and with the radar transmitter on.

FIGS. 8A, 8B, 8C, 8D are SPGR-based continuous golden-angle radial images by breath-hold, free breathing, radar gating, and bellows gating, respectively.

DETAILED DESCRIPTION OF THE INVENTION

Figures 1A, 1B, 1C, 1D:
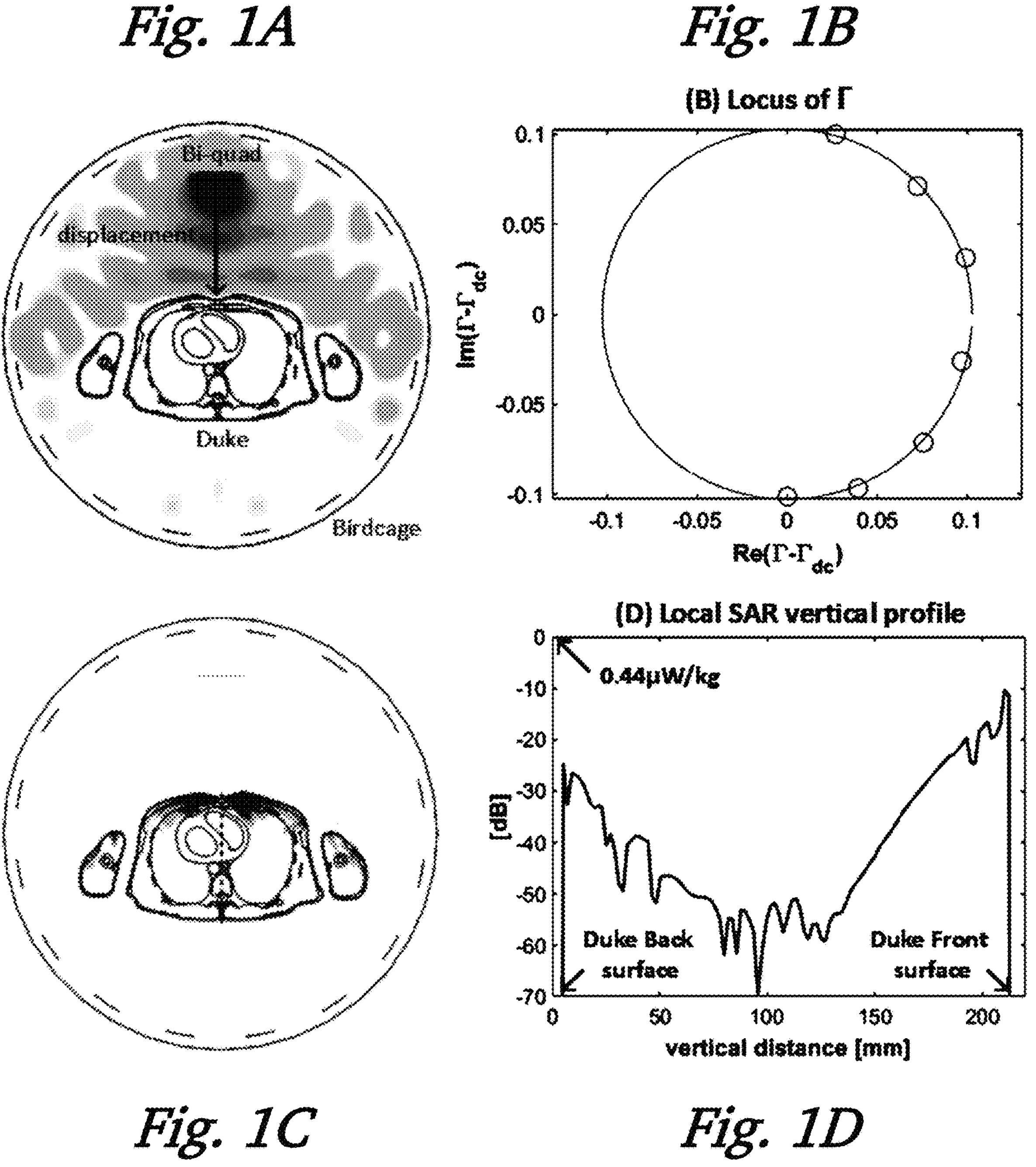
FIG. 1A is a cross-sectional plot of a 2D electric field distribution showing standing wave patterns in the front region of chest wall.
FIG. 1B is a graph showing the locus of antenna input reflection points on the complex plane.
FIG. 1C is a cross-sectional plot of a local SAR distribution showing dominant power deposition in the front chest wall region.
FIG. 1D is a graph of local SAR value as a function of vertical distance.

Embodiments of the present invention provide techniques for non-contact retrospective respiratory gating and cardiac sensing using continuous wave Doppler radar deployed in an MRI system. The techniques may be implemented using a software defined radio configured for continuous wave radar at 2.4 GHz or other microwave frequencies to detect in-vivo respiratory and cardiac time scrolled signals. A radar front-end system arrangement, along with spectral isolation and narrow bandwidth of operation, enable MRI compatible and interference-free motion sensing. The signal-to-noise-ratio degradation by the radar integration was within 4.5% on phantom images. We confirmed that in-bore retrospective motion correction using CW Doppler radar is feasible without constraining the MRI system. In-bore radar signal demodulation is verified with full electromagnetic simulations, and its functionality is validated on a testbench with three normal volunteers and within the MR bore with two normal subjects. The technique can replace or complement existing sensors which are difficult to apply for certain patient populations.

In an illustrative embodiment, a CW radar system is designed for a 3T MRI scanner to provide non-contact respiratory and cardiac rate sensing. A software defined radio (SDR) is configured in a multi-input single-output mode (MISO: two channel receive, single channel transmit). Radar data acquisition is triggered by the scanner TTL signal at start-of-scan to acquire in-vivo cardiopulmonary motion data during radial trajectory MRI scans. Radar-based breathing and cardiac rate sensing is tested in volunteers versus ECG on a testbench, and versus PPG and bellows thereafter within the MRI bore.

Signal Model

Conventional CW Doppler radar transmits a monotone sinusoidal wave and receives phase-modulated backscattered waves from a static or moving object. The demodulated, reflected signal $\Gamma(t)$ includes multiple phase terms yielding:

$$\Gamma(t) = A_r \cdot \exp\left[j\frac{4\pi d(t)}{\lambda} + j[\phi_0 + \Delta\theta(t)]\right] + \Gamma_{dc}. \quad (1)$$

The signal equation describes an arc on the complex plane, and centered at $\Gamma_{dc}$. The latter arises from static clutter, antenna mismatch and from IQ offsets in the receive chain including direct transmit-receive leakage. The wave amplitude $A_r$ will cause a spiral in/out for large motion in the antenna direction or for significant near field interaction. Phase arguments include static phase shift $\phi_0$ by electronic phase delay in the RF front-end, residual phase noise $\Delta\theta$ of the local oscillator (LO), and the slow motion of a locally plane surface at distance d(t). The distance term accounts for group delay of the round-trip traveling wave over a nominal gap $d(t)=d_0+\Delta d(t)$ between a radar antenna and reflecting surface.

Residual phase noise refers to the phase difference of the transmit-receive LO made by the round trip traveling wave duration in free space. This phase difference is nearly negligible according to the range correlation effect for "short-range" sensing of a few meters or less. MRI in-bore sensing, with radar wavelengths of 125 mm at 2.4 GHz, and bore diameters under a meter, meet this condition. While range correlation applies directly to direct IQ demodulation (zero IF or quadrature detection), in the case of SDRs, use of a coherent low IF receive approach (Rx LO offset), can also alleviate noise obstruction at the Rx LO by avoiding interfering LO noise spectra around the carrier without compromising detection efficiency. This approach turns out to be effective to deal with LO discrepancy between transmit and receive of the SDR in use.

Doppler radar behavior in the MRI bore environment can be further estimated by a full 3D finite difference time domain (FDTD) electromagnetic (EM) simulation. As detailed next, simulations also replicate the arc locus of Eq. 1 and indicate that the dominant sensing mechanism pertains to skin surface motion within the antenna beam, as much of the reflected wave comes from the air-skin interface at 2.4 GHz. If the reflected signal $\Gamma(t)$ is corrected for offsets and normalized to incident power, the Doppler signal can equivalently be viewed as an impedance modulation in network analysis since $Z=Z_o(1+\Gamma)/(1-\Gamma)$. In addition, local specific absorption rate (SAR) distribution within a human phantom by radar transmit easily meets any EM exposure limits within the bore.

The MRI bore presents a more electromagnetically complex environment than is typically assumed for Eq. 1. We first assessed its validity for MRI by Sim4Life FDTD modeling (ZurichMedTech ZMT) of a 16 leg high-pass birdcage with a shield conductor radius of 370 mm and a numerical human phantom (Duke-32 yr male, ZMT). Motion induced phase modulation was emulated by sweeping a bi-quad antenna to subject gap distance from 170 mm to 200 mm in 5 mm step sizes. This produced 7 discrete antenna input reflection coefficient (Γ) values, creating a locus of points on an arc that represented group delay variations generated by displacement.

FIGS. 1A-1D show simulation results using Sim4life FDTD of in-bore 2.4 GHz Doppler radar and local specific absorption rate (SAR) estimation. Antenna-subject gap distance is swept from 170 mm to 200 mm to emulate displacement group delay. FIG. 1A shows a 2D electric field distribution at 2.4 GHz on a representative axial numerical slice with a 200 mm gap, illustrating standing wave patterns in the front region of chest wall, dominated by skin-surface reflections. Standing wave patterns can be observed in the gap region, indicating that antenna S11 (ie Γ) and input impedance varies with gap distance given the shallow field penetration within Duke at 2.4 GHz.

FIG. 1B is a graph of after DC offset correction, showing that the locus of antenna input reflection (Γ or S11) points (small circles) still forms an arc on the complex plane as is typical for CW radar. The DC offset was corrected to locate corresponding input reflections, conforming to an origin centered arc, which demonstrates that conventional Doppler phase modulation will be expected within the bore.

FIG. 1C shows a local SAR distribution illustrating dominant power deposition in the front chest wall region, and maximum local SAR value of only 0.44 μW/kg. The simulated local SAR distribution in FIG. 1C shows relatively higher RF power deposition in the front periphery region of the chest. For an operating radar transmit power of 0.23 μW, the maximum local SAR value is a mere 0.44 μW/kg, as shown in the local SAR profile of FIG. 1D. Given that simulated maximum local SAR is negligible relative to the regulatory local limit (10 W/kg) for MRI normal operation (International Electrotechnical Commission IEC 60601-2-33), radar SAR will have no impact on exposure safety.

Figure 2A:
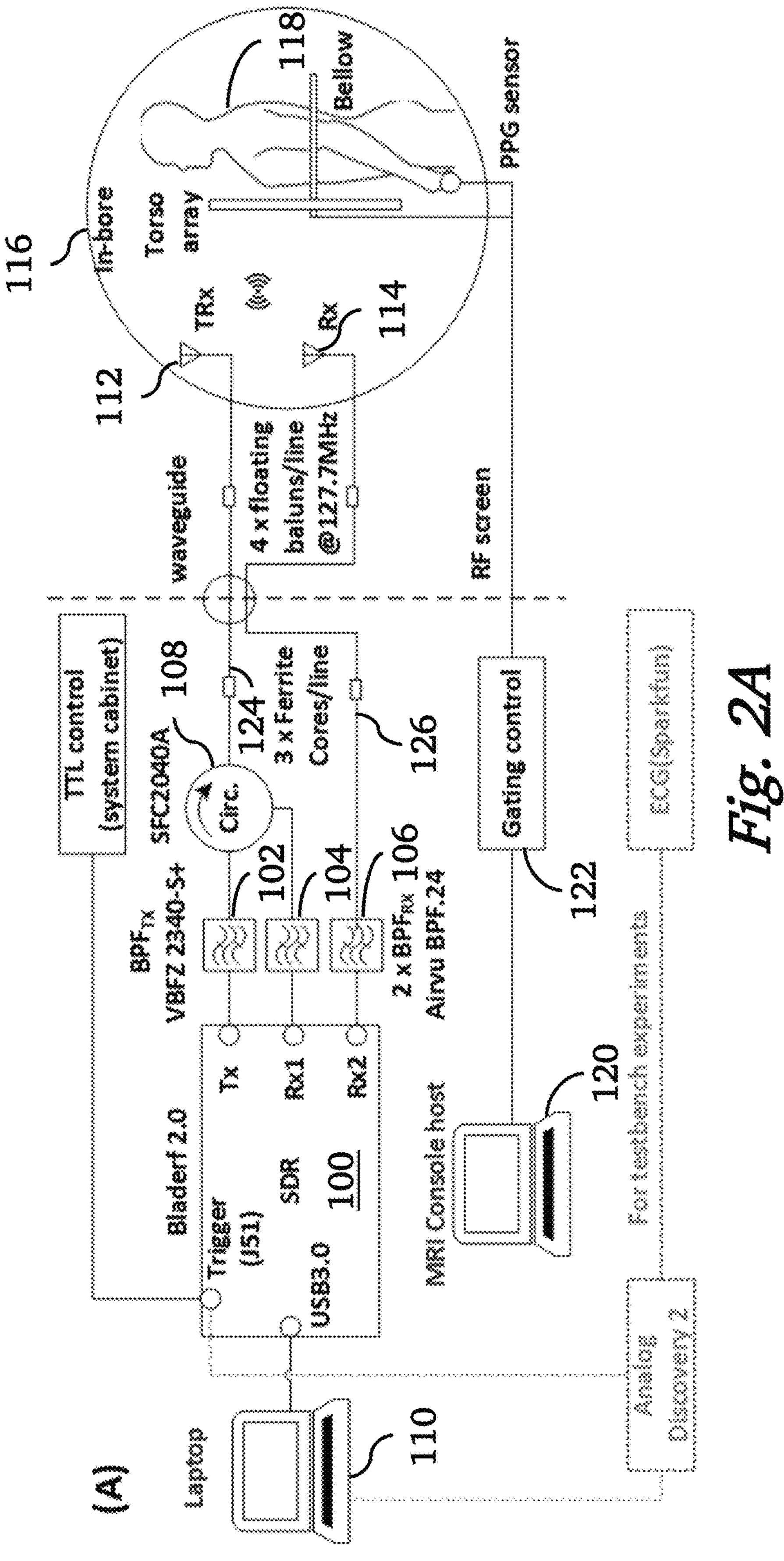
FIG. 2A is a schematic diagram of a CW radar system according to an embodiment of the invention.
Figures 2B, 2C, 2D, 2E:
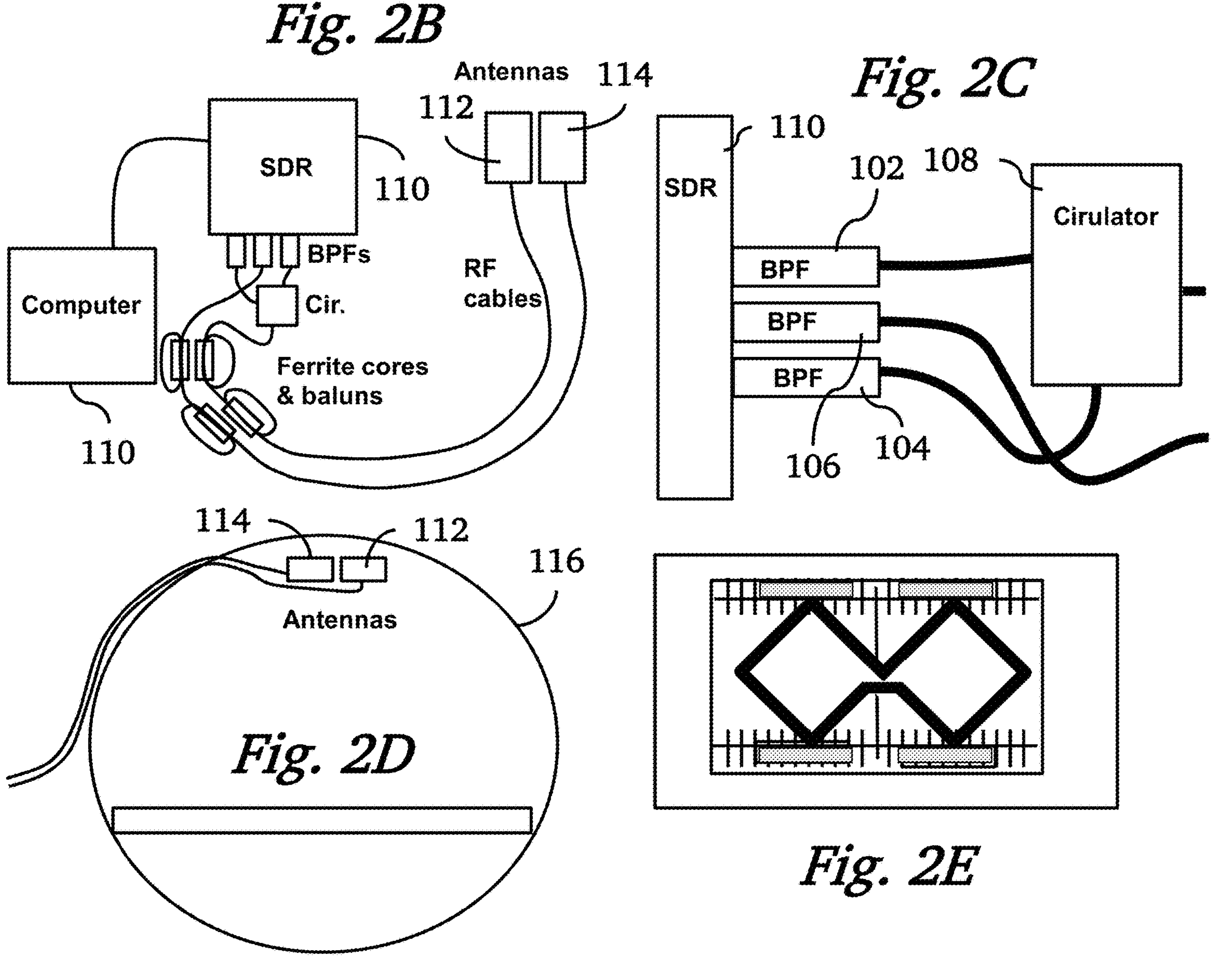
FIG. 2B is a diagram showing a physical realization of the system of FIG. 2A.
FIG. 2C is a diagram showing details of the SDR circulator and bandpass filter of the embodiment shown in FIG. 2B.
FIG. 2D is a diagram showing the in-bore antenna integration of the embodiment shown in FIG. 2B.
FIG. 2E is a diagram showing the directional antenna of the embodiment shown in FIG. 2B.

FIG. 2A shows a schematic diagram of a radar system according to an embodiment of the invention. The radar system in this illustrative embodiment was constructed using an SDR 100, band-pass filters (BPFs) 102, 104, 106, a circulator 108, two in-house bi-quad antennas 112, 114 and respective cables 124, 126, and a digital computer 110. A diagram of 2.4 GHz single channel transmit, dual channel receive radar system components is shown in FIG. 2B. The SDR circulator and bandpass filter connections are detailed in FIG. 2C. At the ports of SDR 110, three band-pass filters 102, 104, 106 (a VBFZ2340-S+ at Tx, two Airvu BPF.24 at Rx) were used at the Tx and Rx ports to suppress MRI RF excitation power coupling into the SDR. A circulator (SFC2040A, Fairview Microwave) provided about 26 dB isolation between the received wave and direct transmit leakage. Inserting the BPF along the Tx path had significant effect on antenna sensitivity, and sensing performance. Putting a BPF right at the SDR Tx port followed by the circulator provided the isolation in transceiver antenna operation.

The SDR 100 (bladeRF 2.0, Nuand) is a two channel Tx/Rx software-defined radio based on the Analog Devices AD9361 and Intel Cyclone V FPGA. The radar acquisition parameters were set by the bladeRF-cli application interface with SDR data acquisition triggered by an MRI start-of-scan signal. It was configured for continuous single channel transmit at 2.4 GHz and dual channel receive with a 50 kHz offset between the RX and Tx local oscillators (LO). The Rx LO offset helped avoid gain instability from on-chip LO crosstalk influencing internal offset correction circuits. The radar transmit power, with a specified transmit gain of 39 dB, was measured to be 0.23 μW at the antenna terminal using a spectrum analyzer (CXA Signal Analyzer, N9000A, 9 kHz-7.5 GHz, Agilent Technologies). Both receiver gains were set at 36 dB, 200 kHz bandwidth, 521 ksps sample rates. Automatic gain control (AGC) was disabled.

One of the directional bi-quad antennas 112, 114 is shown in FIG. 2E. The 2.4 GHz bi-quad antenna uses a back-plate reflector to enhance forward directivity toward the target subject. The bi-quad is effectively two full wave loops in parallel, but here is electrically shortened by copper tape strips acting as capacitive top-loads. The gap of about 1.5 cm or λ/8 between the antenna reflector and bi-quad element, rather than being the ideal λ/4, was adjusted for return loss less than 20 dB at the operation frequency.

The in-bore antenna integration for cardio-respiratory sensing is shown in FIG. 2D Inside the MRI bore 116, two bi-quad antennas 112, 114 were attached to the bore ceiling, adjacent to each other, symmetric with iso-center, and above the subject's landmark (LM) position. These antennas were remotely connected by RF coax cables to the bladeRF, located in the console room. To suppress common mode current, four in-house floating cable baluns (inside scan-room) and three commercial ferrite cores (outside scan-room) were inserted on each 7.2 m coaxial cable. Common mode current suppression was important for reliable SDR operations-without ferrite cores and baluns, the bladeRF easily faulted. To prevent RF background noise, the bladeRF shield was connected to the scan-room ground by a copper wire.

During MRI scans, PPG sensors and respiratory bellows used to measure auxiliary vital signs signals. For development purposes, a radar testbench was also constructed to explore close proximity antenna placement prior to MRI deployment. The radar was configured similarly, but here, an AD8232 ECG board (Sparkfun) provided simplified cardiac signals digitized via an Analog Discovery 2 (Digilent). In this case, the ECG acquisition was triggered by the SDR.

Although this embodiment illustrates the principles of the invention, there are various other ways the invention may implement the same principles. For example, a directional coupler could be used instead of a circulator, a wireless link rather than RF coaxial cables, and another configuration of RF front-ends depending on the system integration location whether within a magnet bore or a remote place somewhere in the system cabinet room. Also, TRx and/or multiple Rx antennas could be integrated into the MRI whole body coil.

Regarding the radar antenna arrangement, besides proximal position near subject motion there is a preferable antenna location which provides minimum EM coupling between whole body resonator and radar system, namely, the center of the whole body volume coil between two adjacent rungs of the birdcage.

Signal Processing

Figure 3A:
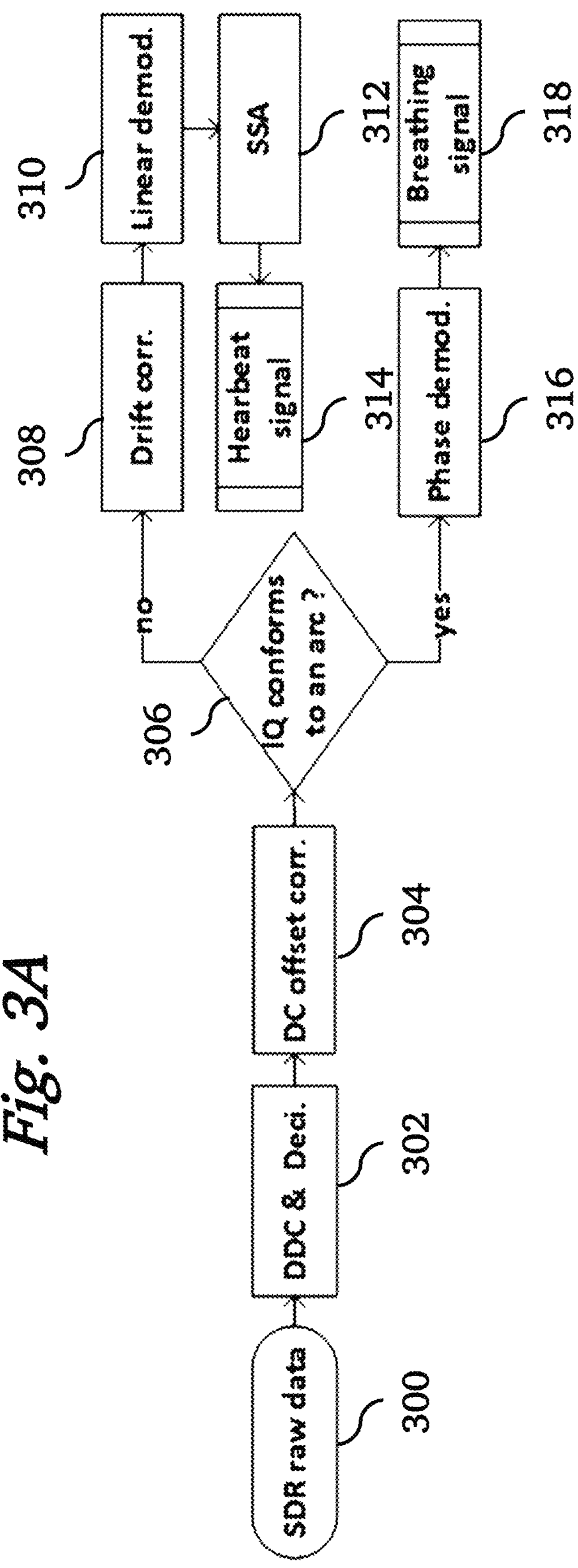
FIG. 3A is a flow chart outlining post-processing steps used for extracting vital signals from radar data.

FIG. 3A shows the post-processing steps of radar time series for the two common vital signs signal extraction schemes. First, SDR radar raw data 300 is digitally down-converted and decimated 302, and then DC offset corrected 304. More specifically, SDR radar data are first numerically demodulated with a 50 kHz offset from the Tx LO, and subsequently down-converted and decimated to 20 Hz bandwidth by a digital down converter (DDC) MATLAB subscript.

Depending on trajectory span 306, phase or linear demodulation is selected. MATLAB pseudo code listings for phase and linear demodulation are shown in FIGS. 3B, 3C, respectively. The linear demodulation includes steps of drift correction 308, linear demodulation 310, and singular spectral analysis (SSA) 312 to produce a heartbeat signal 314. The phase demodulation 316 produces a breathing signal 318.

The linear demodulation first subtracts the complex mean, then finds the rotation via principal components analysis (PCA) to align the complex time-series along the pure real axis. Specifically, covariance terms for the time series $x_n+jy_n$ are computed such as:

$$\sigma_x^2 = \frac{1}{N}\sum_{n=1}^{N}(x_n-\overline{x})^2,\ \sigma_y^2 = \frac{1}{N}\sum_{n=1}^{N}(y_n-\overline{y})^2, \tag{2}$$

$$\sigma_{xy} = \sigma_{yx} = \frac{1}{N}\sum_{n=1}^{N}(x_n-\overline{x})(y_n-\overline{y}), \tag{3}$$

followed by the eigenvalue decomposition with SVD, $$\begin{bmatrix} \sigma_x^2 & \sigma_{xy} \\ \sigma_{xy} & \sigma_y^2 \end{bmatrix} = U\Lambda U^T. \tag{4}$$

The column vector of U corresponding to the largest eigenvalue in A is the principal axis for projection.

Phase (i.e., arctan) demodulation instead attempts to fit an arc of radius A r and origin $\Gamma_{dc}$ to Eq. 1 and subsequently quantify group delay displacement changes. Parameters $A_r$ and $\Gamma_{dc}=x_o+jy_o$ are optimized so data $\Gamma_n=+jy_n$ fall on a circle $$(x-x_o)^2+(y-y_o)^2 = A_r^2 \tag{5}$$

and then the relative distance is quantified from the arc angle:

$$d_n = \frac{\lambda}{4\pi}\angle[\Gamma_n-\Gamma_{dc}]. \tag{6}$$

The $\Gamma_{dc}$ DC offset correction compensates for IQ offsets, transmit leakage and static clutter.

For small displacements such as breath-hold heartbeat sensing, slow drift can mask obscure signal peaks. An optional digital high pass filter (HPF) with 0.5 Hz cutoff (FIG. 3C) can block signal drift, but capture a typical resting heart rate. This assumption may exclude abnormal conditions like ectopic heartbeats or arrhythmia. For normal adult respiratory sensing at 2.4 GHz, drift is not a concern. Although there exists a preferable demodulation scheme depending on scale of displacement, we note that linear demodulation at 2.4 GHz works well for both breathing and heartbeat sensing especially when complex trajectories have a narrow angular arc span. In contrast, phase demodulation is limited to signals forming a wider angular arc after DC offset correction.

As a final step for heart-rate sensing, singular spectral analysis (SSA) is applied over the breath holding window to suppress residual trend and background noise for effective signal peak detection. The number of reconstructed principal components in SSA were empirically determined (five) for clear delineation of signal peaks. To perform SSA on the now demodulated N-point real sequence $x_1:x_N$, a window length M<N/2 is chosen to construct a trajectory matrix. Here, M was set to cover about 3 periods of the subject's cardiac cycle. The trajectory matrix X is constructed of K=N−M+1 rows and M columns such that row $X_k=x_k:x_{k+M-1}$. The trajectory matrix X has a Hankel or Toeplitz form depending on construction, and can be decomposed by SVD: $X=U\Sigma V^T$. The M singular values are grouped to isolate trend, oscillatory, and noise terms. Subsequently, a subgroup of a:b singular values is selected to create a detrended, denoised trajectory matrix $$\hat{X}_{a:b} = \sum_{m=a}^{b}\sigma_m u_m v_m. \tag{7}$$

The time series is recovered by diagonal averaging. The SSA processing time using MATLAB was within a second with an Intel core i7 loaded computer (memory 16 GB). Respiratory and cardiac synchronization points were identified at high peaks of the radar signals using a MATLAB function, "findpeaks".

Testbench Experiments

To assess potential in-bore sensing locations, initial validation and post-processing tests, testbench experiments were setup and conducted. FIGS. 4A-4D show four testbench antenna placements and respective radar signals over 20 s normalized to the same scale during free breathing and breath holding.

Figures 4A, 4B, 4C, 4D:
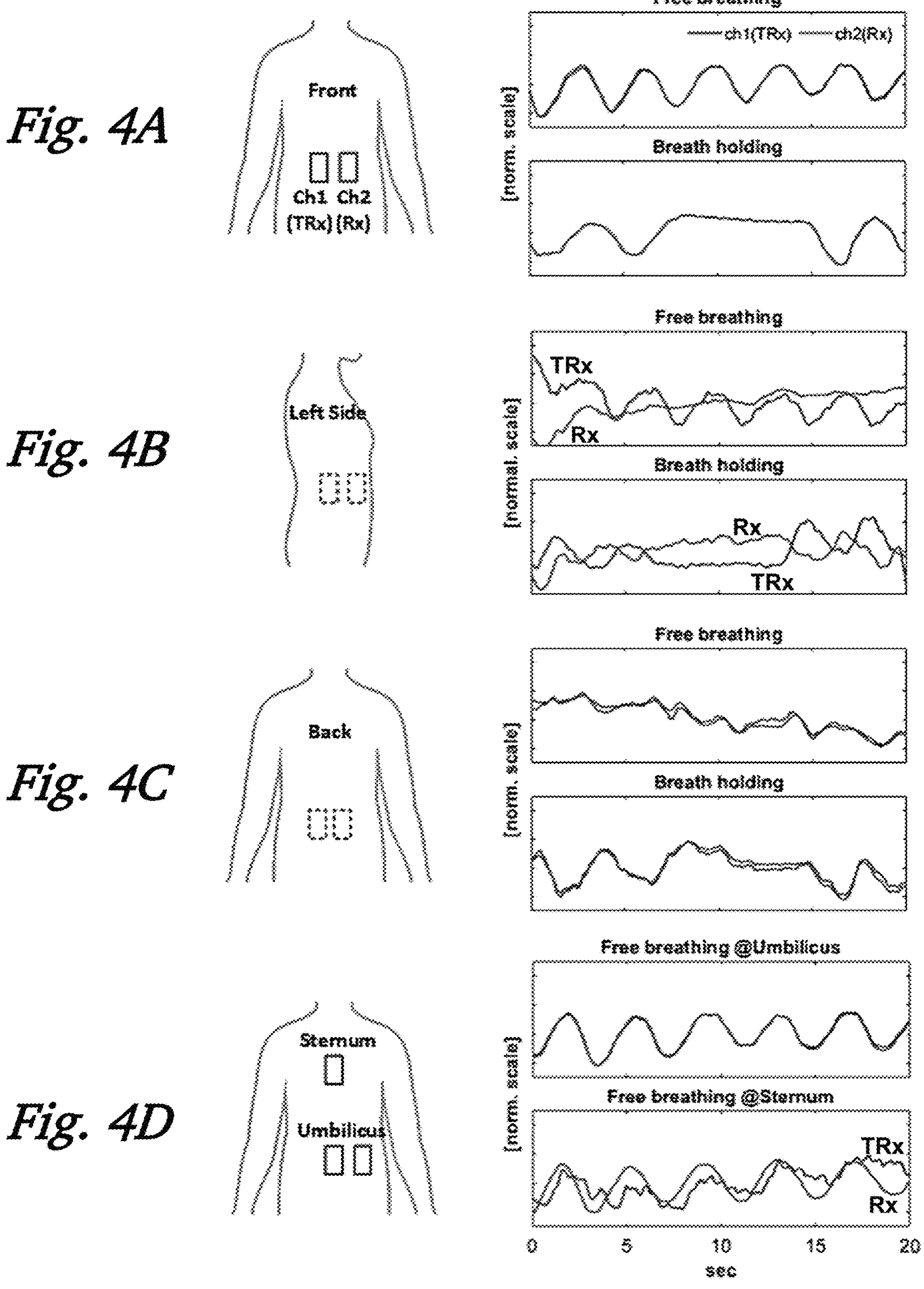
FIGS. 4A, 4B, 4C, 4D show free breathing and breath holding graphs for four different antenna placements, respectively.

FIGS. 4A, 4B, 4C show measurement schematics for three bi-quad antenna arrangements. Two antennas were positioned over the front, shown in FIG. 4A, the side, shown in FIG. 4B, and the back, shown in FIG. 4C, of the subject torso. With each setup, radar depth sensitivities were qualitatively assessed for free breathing and breath-holding conditions. In addition, signal sensitivity at two local regions over the umbilicus and mid sternum were investigated relative to the fixed antenna placement over the lower abdomen, as shown in FIG. 4(D). This measurement was conducted under regular free breathing conditions. For all cases, the antenna distance to the subject was about 20 cm without an intervening MRI anterior array.

In FIG. 4A, both channels demonstrate clear breathing signals, whereas FIG. 4B and FIG. 4C are ambiguous except those from the lateral anterior antenna. FIG. 4D shows the free breathing signal dependence on antenna location relative to local body part. About 20 cm of gap existed between antenna and body surface for all cases.

Maximum sensitivity for breath/breath-held conditions arose when the antenna beam was exposed to the radial front abdominal wall motion as in FIG. 4A. Similar sensing performance was observed for lateral movement from the superior antenna in FIG. 4B, whereas back side antenna placement produced ambiguous breathing patterns as in FIG. 4C. Hence, within the MRI, antenna alignment with respect to either radial or lateral abdominal wall movement is desirable for respiratory sensing. FIG. 4D demonstrates that antenna placement over the umbilicus produced clear free breathing pattern on both channels. Over the sternum, higher frequency signal fluctuations were observed, implying antenna placement over the region of interest is required.

Heart rate sensing was explored by twelve sets of breath-hold cardiac measurements (4 sets on each of three volunteers). Two adjacent antennas were placed over the left side of the mid sternum with an antenna-subject separation of about 20 cm to target where the most prominent heart impulse is observed. A three lead ECG (AD8232, Sparkfun) was synchronized with radar measurements during each breath-hold. The free-running ECG data was first stabilized with the subject sitting still and recorded using a data logger (Analog Discovery 2.0, Digilent). The bladeRF trigger pin J51, and the "trigger j51 tx fire" command gated the ECG acquisition. Both data-sets were recorded over a 20 s-time window.

ECG synchronization points were retrospectively extracted at the R peaks, and those of radar at the high peaks of the SSA time series. Based on identified ECG/radar peak points, peak-to-peak (P-P) intervals were calculated and compared. Beats per minute (BPM), average radar peak delay referenced to R peaks, and P-P root mean square error (RMSE) in ms are summarized in Table 1.

The heart rate estimation from breath-hold data agree with those of the ECG. The overall maximum BPM and P-P error were 0.85 bpm and 162.7 ms, respectively. The estimated radar (high) peak delay referenced to ECG R peak ranged from 57% to 85% of the average R-R interval, depending on subject BPM. Overall average BPM difference and P-P error were within 0.28 bpm and within 49.6 ms.

Figures 5A, 5B, 5C, 5D:
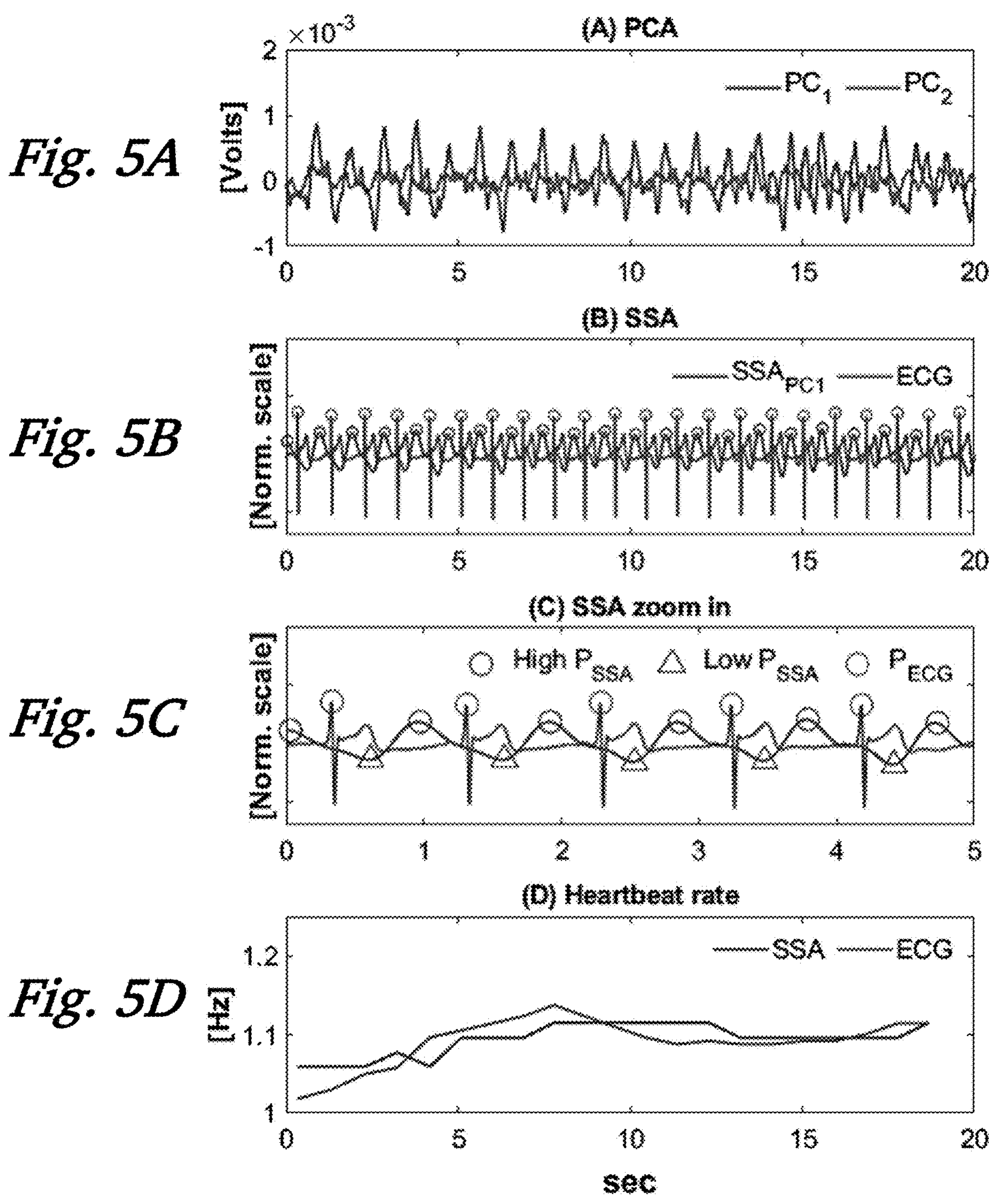
FIGS. 5A, 5B, 5C, 5D show graphs of PCA, SSA, SSA detail, and heartbeat rate, respectively.

FIGS. 5A-5D are graphs illustrating a testbench demonstration of linear demodulated radar signal profiles for heart rate estimation. PCA (FIG. 5A) and voltage drift correction extracts the maximum variance signal out of two complex channels. Next, SSA (FIG. 5B) denoises the linear demodulated signals for peak detection. The estimated radar low and high peaks in FIG. 5C are parked around the T and P wave peak, respectively. The radar heartbeat rate shown in FIG. 5D follows those of the ECG, resulting in a P-P RMSE of 17.1 ms.

The example of cardiac rate estimation in FIGS. 5A-5D shows radar peak delay relative to ECG R peaks. The radar signal was reconstructed by linear demodulation and SSA was used to denoise signal for reliable peak identification. The estimated radar low peaks are parked close to the ECG T wave, corresponding to the ventricle volume change (Systole to Diastole), whereas radar high peaks occur close to the P wave peak in the atrial contraction.

MRI System Integration and Feasibility Test

Free breathing and breath-held heartbeat radar sensing feasibility tests were conducted. Inside the scan-room, the subject lay in the supine position at the cardiac landmark, supporting a torso anterior array (Air-coil, GE), and beneath an in-table posterior spine array. About 20 cm of gap existed between the antenna and the subject's chest wall. For vital references, the system bellows and PPG pulse sensor were placed on the subject. These system vital signs sensors were recorded by the MRI gating control during SPGR-based scans described later. Among various in-bore vital sensing tests, two representative measurement results are presented in FIGS. 6A, 6B. In-bore radar free breathing, and breath-hold heartbeat signals are shown by conventional phase and linear demodulation, respectively.

Figure 6A:
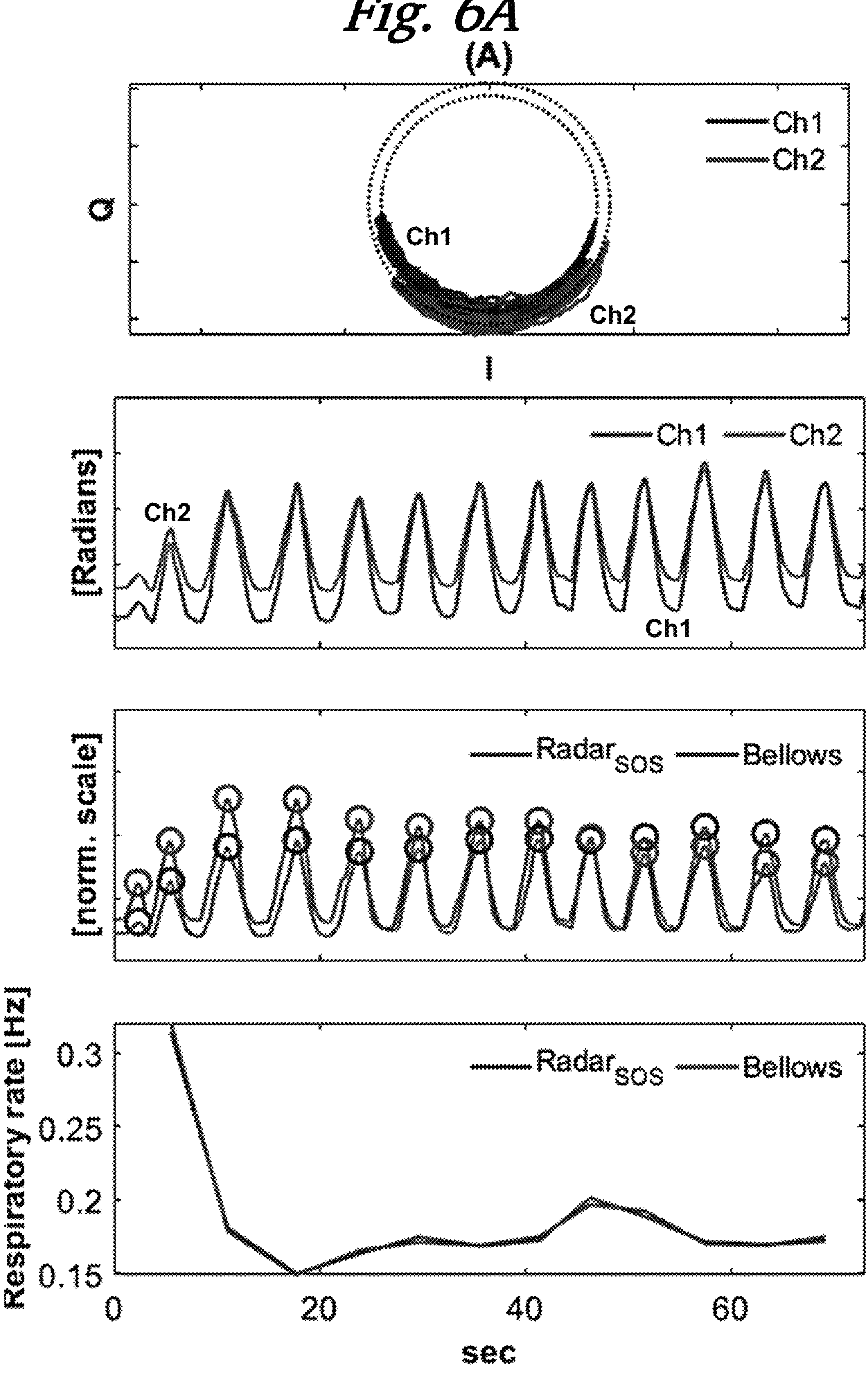
FIGS. 6A, 6B show, for conventional phase and linear phase, respectively, graphs of in-bore radar free breathing measurements and breath-hold heartbeat signals.

First, two channel complex free breathing data form the IQ plot after DC offset correction. As shown in FIG. 6A, two channel complex signals trace out an arc, such that phase demodulated signals align. Identified peaks and their combined sum of squares signal closely matches the bellows with P-P RMSE of 76.1 ms. The locus of each individual channel conforms to an arc, suggesting feasibility of phase demodulation for MRI radar data. The sum of squares (sos) combined time series of each phase demodulated signal was in good agreement with the bellows in terms of identified signal peaks over 70s. The measured radar amplitude did not exactly coincide with the bellows, which may be attributed to the different

TABLE 1

Twelve sets of breath-hold cardiac rate measurements (4 sets on each of three subjects) validated with a time-aligned reference ECG on a testbench. Heart rates in BPM, average radar peak delay, and percent P-P errors are summarized.

| | BPM | | Avg Pk Del(ms)* | P-P RMSE(ms) |
|---|---|---|---|---|
| | ECG | SSA | SSA(Std) | SSA |
| Vol. A | | | | |
| 1 | 68.42 | 68.53 | 564.5 (16.0) | 13.2 |
| 2 | 65.75 | 65.82 | 581.4 (15.4) | 15.1 |
| 3 | 70.90 | 71.06 | 656.7 (50.5) | 44.4 |
| 4 | 65.49 | 65.66 | 571.0 (27.3) | 17.1 |
| Ave. | 67.63 | 67.77 | 593.4 (27.3) | 22.5 |
| Vol. B | | | | |
| 1 | 70.05 | 70.15 | 575.4 (46.5) | 79 |
| 2 | 71.12 | 71.06 | 530.1 (74.1) | 84.8 |
| 3 | 71.32 | 70.47 | 519.3 (119.6) | 162.7 |
| 4 | 70.43 | 70.05 | 491.3 (45.9) | 53.7 |
| Ave. | 70.73 | 70.43 | 529.0 (71.5) | 95.1 |
| Vol. C | | | | |
| 1 | 85.73 | 85.47 | 536.6 (55.1) | 34 |
| 2 | 91.14 | 91.35 | 521.3 (19.4) | 14.8 |
| 3 | 86.88 | 86.7 | 563.4 (35.4) | 40.1 |
| 4 | 90.16 | 89.36 | 566.9 (35.5) | 36 |
| Ave. | 88.48 | 88.22 | 547.05 (36.4) | 31.2 |

*Radar (high) peak delay was referenced to ECG R peaks.

sensing physics of the two systems. Despite the sensing system differences, the calculated P-P respiratory rate matches well between the two, resulting in a RMSE of 76.1 ms.

Figure 6B:
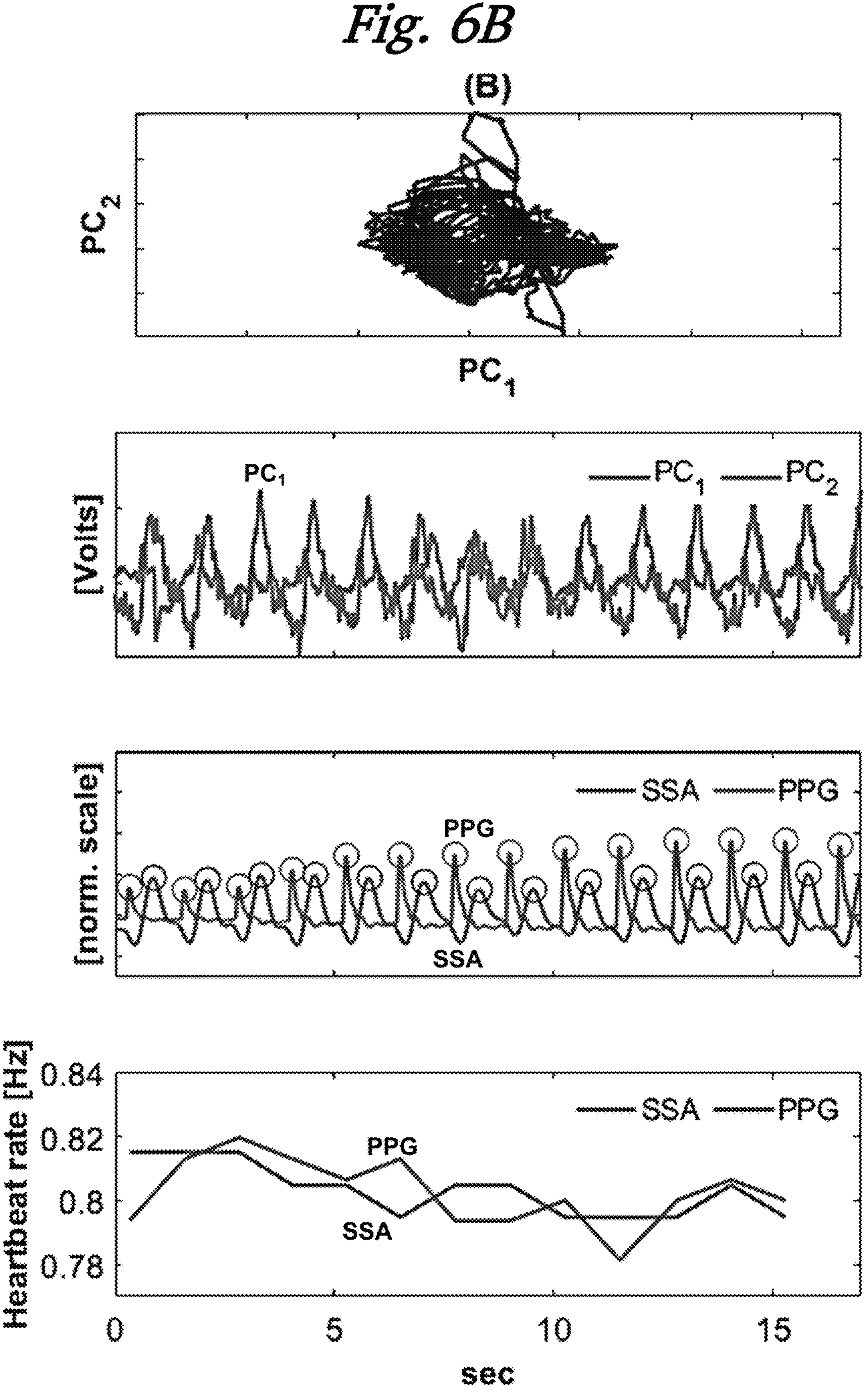

The second in-bore heartbeat sensing experiments were conducted during a breath-held scan. In FIG. 6B, the linear demodulated heartbeat rate matches the MRI PPG sensor with P-P RMSE of 16.2 ms. The trace of two significant principal components are plotted after voltage drift correction, showing a more irregular trace. After linear demodulation, SSA is applied to the first principal component to delineate the heartbeat peak. Identified peak points and time varying heart rate between the SSA and PPG signals resulted in good agreement with a P-P RMSE of 16.2 ms.

Compatibility and Interference

To investigate the influence of radar operation on MRI, image quality (IQ) was assessed by obtaining SNR maps of three plane phantom images (axial, sagittal, coronal) with an anterior body (Air-coil, GE) and a posterior spine coil (In table coil, GE). Two vendor-supplied (GE) rectangular block phantoms were used for this experiment. SNR maps were calculated by root sum of square (RSS) combining for three different system setups: a default without the radar system (baseline), and with the radar system transmit on and off. In each case, three-slice noise images were independently obtained using a system control variable to calculate a noise covariance matrix for pixel-by-pixel SNR maps and relative noise power. Average SNR values within the ROI (masked phantom region) and relative average noise power were quantified with radar on and off, and compared to the baseline. The relative average noise power was based on average diagonal terms for each noise covariance matrix, normalized by the baseline. Quantified numbers are summarized in Table 2.

Figures 7A, 7B, 7C:
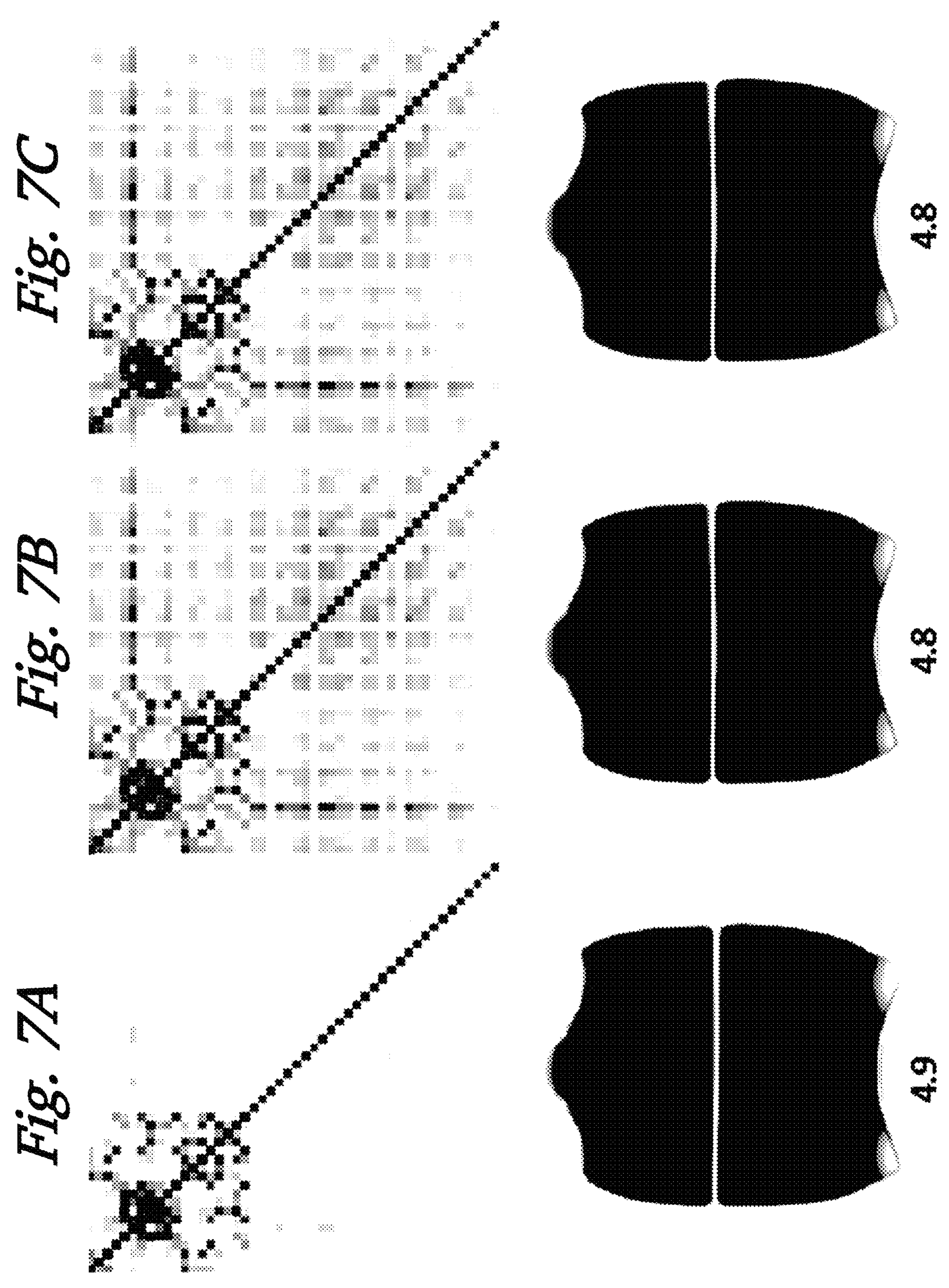

In image quality assessments, FIGS. 7A-7C show colormaps of the noise correlation matrices and SNR maps on the coronal plane with baseline and radar on and off as an example. A single slice fast GRE sequence (TR 34 ms, TE min, FOV 50 cm, Slice thickness 5 mm, Flip angle 30, BW/pixel 244.1 Hz, Matrix 256×256) was used for this evaluation.

Noise covariance matrices without the radar system (baseline) are shown in FIG. 7A. Noise covariance matrices with the radar Tx off are shown in FIG. 7B and with the radar Tx on in FIG. 7C. The variation in noise characteristics due to the radar system integration was minimal. A slight correlated noise enhancement was observed with the minimum SNR degradation less than 3%. All measurements were performed with an MRI anterior array (Air-coil, GE) and a posterior spine coil (In table coil, GE).

As shown in Table 2, the quantified MRI SNR degradation by the radar integration was within 5%, compared to the baseline. The image SNR changes between radar on and off were within 1%, indicating that radar operation has little effect on image quality. The estimated percent average noise power increase by radar Tx on and off were less than 10%, compared to the baseline. With these levels, we were not able to visually discern image degradation either on phantom or volunteer images. In FIGS. 7A-7C, there was a slight correlated noise increase in the first row with radar integration, but this did not degrade SNR significantly (SNR degrades by 2.8%), supporting MR compatibility of radar. However, we noticed that poor cable handling could have a significant effect on system noise, requiring careful RF cable handling within the bore.

The influence of the imaging coil placement between subject and radar antenna was discovered to be a significant aspect of radar integration. The regular anterior coil placement over the torso did not influence the radar signal significantly. Although a coil conforms to a moving surface, the mechanical coupling between coil and subject may matter since it certainly acts as a scatterer.

TABLE 2

Summary of calculated three slice average SNR numbers within a phantom ROI and the percent average noise power increase with radar on and off states. The baseline refers to the default system prior to radar integration.

| | $SNR_{ROI}$ | | | % $P_{noise}$ increase | | |
|---|---|---|---|---|---|---|
| | Axial | Coronal | Sagittal | Axial | Coronal | Sagittal |
| Baseline | 7.91 | 4.9 | 12.06 | | | |
| Radar Off | 7.54 | 4.8 | 12.04 | 9.98 | 8.01 | 8.16 |
| Radar On | 7.58 | 4.8 | 12.03 | 6.78 | 8.75 | 8.45 |
| % Max dif. | 4.43 | 2.80 | 0.54 | | | |
| % On-off dif. | −0.53 | 0.08 | 0.00 | −2.91 | 0.68 | 0.27 |

"−"sign convention denotes noise power decrease in radar-on, compared to radar off case Retrospective Respiratory Gating Applications For radar motion correction evaluation, we collected 2D and 3D SPGR-based continuous golden-angle radial data from two healthy volunteers (Vol. D & B), respectively. The 2D cardiac images were acquired with TR=4.7 ms, TE=2.2 ms, flip angle=15, slice thickness=6 mm, and total acquired spokes=19200 (1 min 30 s). Similarly, 3D stack of stars abdominal images used TR=4.3 ms, TE=1.6 ms, flip angle=10, slice thickness=5 mm, and total acquired spokes=720 (2 min). To reconstruct the 2D cardiac radial k-space data, multiple cardiac phases were first classified using cardiac triggers by PPG. Then, the half k-space data corresponding to the expiratory phase were processed for gated reconstruction. Respiratory phases were identified by the bellows and the radar. Afterwards, iterative reconstruction was carried out with iGRASP using total-variation (TV) regularization (with λ=0.001) along the temporal axis. To reconstruct 3D stack-of-stars k-space data, the respiratory signals from self-navigation, bellows, and radar were divided into four respiratory phases, individu-ally. Then a soft-gated iterative reconstruction was carried out with a TV constraint in the image domain for each case.

FIGS. 8A-8D show cardiac SPGR-based continuous golden-angle radial images with a breath-hold scan (FIG. 8A), free breathing without gating (FIG. 8B), free breathing with retrospective radar gating (FIG. 8C), and bellows gating (FIG. 8D). The radar gating data is that of FIG. 6A. Both gated images have a similar visual appearance, and delineated the myocardium by reducing motion artifacts. However, when compared to the breath-hold image, the gated reconstruction still exhibits residual blurring in the image. This may be attributed to insufficient sampling data during the expiratory phase with a short scan (11 s).

Figures 9A, 9B, 9C, 9D:
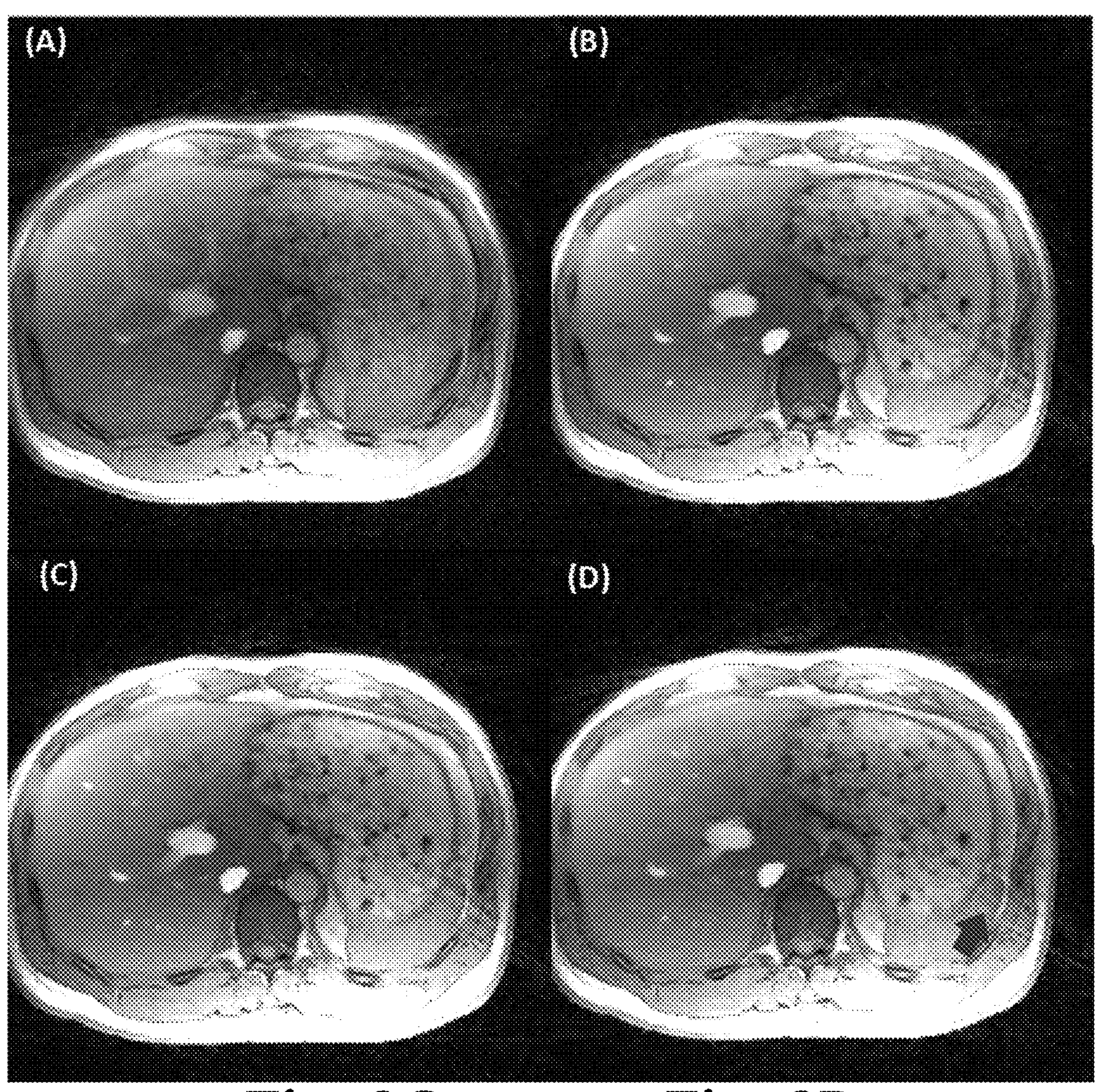
FIGS. 9A, 9B, 9C, 9D are 3D abdominal stack-of-stars SPGR images with, respetively, ungated, bellows gated, self-navigation gated, and radar gated results.
Figure 9E:
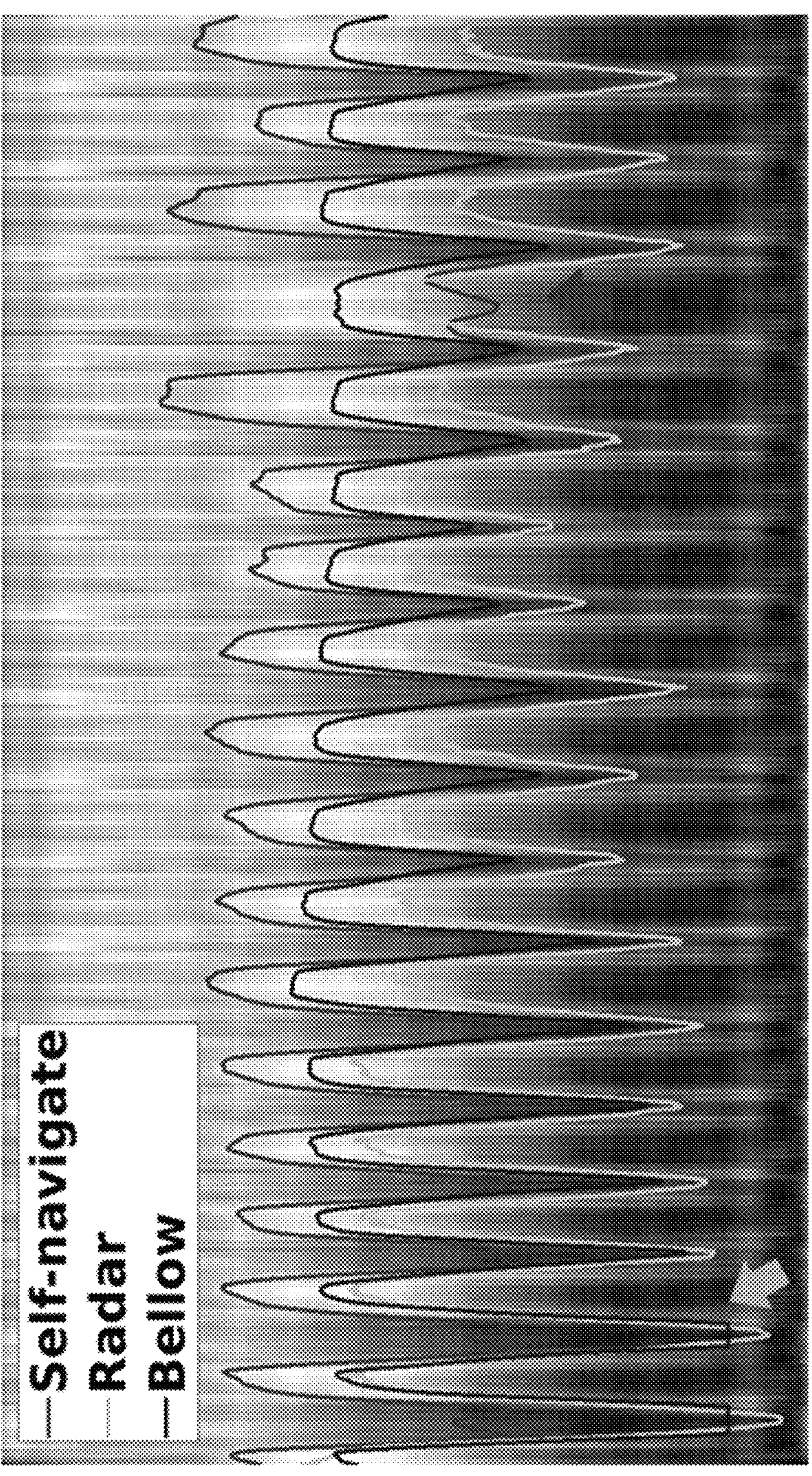
FIG. 9E) is a graph of respiratory motion signals.

FIGS. 9A-9E show free breathing abdominal 3D stack-of-stars SPGR images with ungated (FIG. 9A), bellows gated (FIG. 9B), self-navigation-gated (FIG. 9C), radar gated (FIG. 9D), as well as the corresponding respiratory signals in FIG. 9E. Compared to ungated image (FIG. 9A), the gated reconstruction images (FIG. 9B, 9C, 9D) reveal more anatomical details by incorporating time-resolved motion segments of the respiratory state. In particular, the radar gated image (FIG. 9D) presents reduced streaking artifacts, compared to other navigators. The ungated image (FIG. 9A) has a large amount of motion artifact due to free breathing, resulting in a blurred image that obscures small structure details. The gated images (FIG. 9B, 9C, 9D) present reduced motion artifacts, delineating boundaries of different structures much more clearly. Interestingly, in comparing gated images, the retrospectively radar gated image (FIG. 9D) exhibits reduced streaking artifacts, compared to the others (FIG. 9B, 9C). This may be attributed to the k-space segmentation more precisely provided by the intact breathing signal amplitude of the radar. This evidence suggests that radar temporal signal amplitude varies with displacement and is capable of detecting breathing depth. In contrast, the self-navigated signal shows a missed breathing cycle around 100 s, which can happen occasionally. The signals acquired from the bellows resulted in hard cut-offs in the first two low peaks when the breathing motion was too large. These imperfections may affect k-space segmentation to some extent. Otherwise, the extracted respiratory signals by the three different approaches present good agreement over 123 s in FIG. 9E. The respiratory motion signals in FIG. 9E were all in good agreement. However, the self-navigated signal shows a missing pattern, and the bellows signal shows hard cut-offs in the first two low peaks when deep breathing was present. In contrast, the radar signal demonstrates intact signal amplitude over measurement time.

Radar Sensitivity

Doppler CW radar consumes very low power, very low bandwidth and is easy to implement compared to pulsed radar. The radar transmit power of about a quarter μW (−36 dBm) easily sufficed to quantify cardio-respiratory signals during MRI operations. For a 60 kg subject, this would amount to an extra 4 nW/kg SAR—an infinitesimal amount compared to the 4 W/kg limit of the IEC 60601-2-33 guidelines. This leaves considerable headroom for increasing radar transmit power to enhance cardiac signals or broaden motion sensing coverage with multiple antennas. Signal fidelity also depends on residual phase noise control of the LO. The internal architecture of the SDR IC can cause unstable crosstalk for simultaneous Tx/Rx at the same frequency. Thus, to obtain a phase noise range correlation effect similar to radar employing discrete quadrature demodulators, a small frequency offset was needed. To extract vital signs of periodicity 0.1-10 Hz, offsets exceeding 100 Hz within the SDR demodulation bandwidth worked well for successful baseband signal extraction.

The bi-quad antenna's broadside directivity enhanced sensitivity in the radial direction of surface displacement. Surface tissue (conductivity 1.44 to 1.56 S/m at 2.4 GHz) acts as a moving reflector that modifies round-trip group delay and equivalently, impedance. As expected, antenna locations directly above the chest easily detected respiratory motion, whereas the cardiac sensing area was limited to a relatively small chest wall region.

A harmonic tag may be used for enhancing specific target signals using a spectrally selective demodulation technique. Ka band or mm-wave radar (24-40 GHz) is also expected to boost cardiac sensitivity based on the enhanced doppler effect at higher frequencies for small displacements.

Signal Processing

Conventional phase and linear demodulation remain applicable in the MRI bore for cardiopulmonary sensing, despite the highly reflective environment of the bore. Phase demodulation is superior when the complex baseband IQ trajectory falls on an arc corresponding to cm-scale motion, but is error prone for (sub) mm scale sensing. In the latter case, the IQ locus forms a locally linear or more chaotic trajectory for which linear demodulation was most effective. For either demodulation scheme, temporal resolution of the cardio-respiratory signals depends solely on radar sampling rate and decimation factor, which provides versatility in the choice of sequences for motion gating.

For CW radar, the SSA algorithm was found to be helpful especially when the original radar peaks were ambiguous. SSA is model-free and can act as a data-driven filter. Selecting the embedding window length in two to four target periods sufficed for successful cardiac peak point extractions. In heart rate estimation, the identified radar peaks exhibited significant delay from ECG R peaks, which may be attributed to the surface mechanical response from ventricular volume changes. If single or several abrupt signals occurred, SSA was not quite as effective, requiring the subject be in a static posture. In future, we expect adaptation of multi-channel SSA and independent components analysis (ICA) to further improve robustness and signal separation.

Compatibility and Interference

By judicious use of RF filters to inhibit B1 transmit coupling, MRI sequence operations did not impair radar operation, allowing simultaneous radar signal acquisition. This was aided by the large spectral separation between the radar and Larmor frequencies, as well as the narrow CW demodulation bandwidth. Moreover, no signs of acoustic vibration artifact were observed in the radar signal during the scan. Conversely, the radar system integration had little effect on MRI receive performance, but careful RF cable routing within the bore is required. We observed that poor cable placement could degrade MRI along with noticeable system transmit gain increments. Embedding radar antennas within the body coil is a preferred design approach in some embodiments of the invention. Preferred cable routing is through a minimum electric field region in the center circumference of the birdcage coil. In addition, connecting radar cable shields via a low inductance path to the body coil shield may address common mode current issues.

CONCLUSION

We have described a technique for non-contact in-bore respiratory and heart rate signal acquisition using CW Doppler radar in a 3T MRI. Its feasibility was demonstrated for retrospective respiratory gating applications. A portable, reconfigurable SDR provided sufficient signal fidelity even with sub-μW transmit power at 2.4 GHz to reconstruct cardiopulmonary related signals during MR scan operations. Although radar system operation has minimal effect on MRI system performance, integration requires care in auxiliary radar cable handling and antenna distribution within the body coil. Vital signs Doppler radar sensitivity is exceptional and well suited for integration with MRI scanner clinical workflow.

The invention claimed is:

1. A method using Doppler radar for noncontact sensing of subject motion within a magnetic resonance imaging (MRI) apparatus during an MRI scan, the method comprising:

(a) transmitting by a quadrature radio configured for single channel transmission with a first directional antenna a band-pass filtered continuous wave radio signal at a microwave frequency, wherein the transmitted band-pass filtered continuous wave radio signal is a monotone radio signal, spectrally separated from an MRI Larmor frequency, wherein the first directional antenna is positioned above a target motion-sensing region;

(b) receiving by the quadrature radio configured for dual channel reception with the first directional antenna and with a second directional antenna a band-pass filtered reflected radio signal, wherein the first directional antenna is positioned above the target motion-sensing region, wherein there is a frequency offset between the single channel transmission and the dual channel reception; and (c) detecting the subject motion from the received band-pass filtered reflected radio signal using the quadrature radio implementing Doppler radar; wherein detecting comprises:

(i) digitally down-converting radar raw data by direct IQ demodulation, (ii) correcting for DC offset, and (iii) performing phase or linear demodulation to produce a movement signal;

wherein the first directional antenna is connected to the quadrature radio using a hardware front-end chain comprising first band-pass filter, a second band-pass filter, and an RF coupler; wherein the second directional antenna is connected directly to the quadrature radio using a third band-pass filter, wherein the first band-pass filter, the second band-pass filter, and the third band-pass filter are configured to block MRI RF interference outside the radar operating frequency and mitigate kW-level RF peak power leakage from the MRI apparatus;

wherein the first directional antenna is connected to the RF coupler, wherein the first band-pass filter is positioned between a transmission output of the quadrature radio and an input of the RF coupler, wherein the second band-pass filter is positioned between an output of the RF coupler and a reception input of the quadrature radio;

wherein the second directional antenna is connected to a reception input of the quadrature radio, wherein the third band-pass filter is positioned between the reception input of the quadrature radio and the second directional antenna;

wherein the first directional antenna and the second directional antenna are positioned in a bore of the MRI apparatus and the quadrature radio operates at a transmit power level below 1 mW.

2. The method of claim 1 wherein the RF coupler is a circulator, directional coupler, or hybrid coupler.

3. The method of claim 1 wherein the received band-pass filtered reflected radio signal is a Doppler phase modulated monotone radio signal.

4. The method of claim 1 wherein the quadrature radio uses a receiver local oscillator frequency that is offset from a transmit oscillator frequency.

5. The method of claim 1 wherein the receiver local oscillator frequency offset is within a demodulation bandwidth of the quadrature radio.

6. The method of claim 1 wherein the first directional antenna and the second directional antenna are positioned symmetric with iso-center of a bore of the MRI apparatus, above a subject landmark (LM) position.

7. The method of claim 1 wherein the first directional antenna and the second directional antenna are attached to a ceiling of a bore of the MRI apparatus.

8. The method of claim 1 wherein the first directional antenna and the second directional antenna are embedded within a body coil of the MRI apparatus.

* * * * *